US005543131A

United States Patent [19]

Levy

[11] Patent Number: 5,543,131
[45] Date of Patent: Aug. 6, 1996

[54] HIV-2 STRAINS CAPABLE OF INFECTING HUMANS AND NON-HUMAN PRIMATES, AND INFECTED NON-HUMAN PRIMATES WITH IMMUNE SYSTEM DISEASE

[75] Inventor: Jay A. Levy, San Francisco, Calif.

[73] Assignee: The Regents of the University of California, Oakland, Calif.

[21] Appl. No.: 286,479

[22] Filed: Aug. 5, 1994

[51] Int. Cl.[6] .................................................... A61K 49/00

[52] U.S. Cl. .......................... 424/9.2; 435/948; 435/974; 800/2; 800/DIG. 5

[58] Field of Search .......................... 424/9.2; 435/235.1, 435/948, 974; 800/2, DIG. 5

[56] References Cited

PUBLICATIONS

S. W. Barnett et al. (1994) Science 266: 642–646.

Livartowski et al., "Clinical and Virological Aspects of HIV 2 Infection in Rhesus Monkeys," *Cancer Detection and Prevention* (1992) 16:341–345.

J. McGlure et al., "In Vivo Passage of HIV–2 EHO in *Macaca Nemestrina* results in Persistent Infection, Disease Progression, and Altered Cellular Tropism," *10th Annual Symposium on Non–Human Primate Models for AIDS* (1992), Abstract No. 3.

Stahl–Hennig et al., "Experimental Infection of Macaques with HIV–$2_{ben}$, A novel HIV–2 Isolate," *AIDS 6* (1990) 4:611–617.

Castro et al., "Persistent Infection of Baboons and Rhesus Monkeys with Different Strains of HIV–2," *Virology* (1991) 184(1):219–226.

Desrosiers, R C, "The Simian Immunodeficiency Viruses," Paul, W. E. (Ed.), *Annual Review Of Immunology*, Annual Reviews, Inc.: Palo Alto, California, (1990) 8:557–578.

Donaldson et al., "Redistribution of HIV Outside the Lymphoid System with Onset of AIDS," *Lancet* (1994) 343:382–385.

Frumkin et al., "Acute Infection of Macaca Nemestrina by Human Immunodeficiency Virus Type 1," *Virology* (1993) 195(2):422–431.

Gardner et al., "Animal Models of AIDS," *FASEB J.* (1989) 3:2593–2606.

Hirsch et al., "Simian Immunodeficiency Virus Infection of Macaques: End–stage Disease is Characterized by Widespread Distribution of Proviral DNA in Tissues," *J. Infect. Diseases* (1991) 163(5):976–988.

Hsia et al., "Human Immunodeficiency Virus DNA is Present in a High Percentage of CD4 Positive Lymphocytes of Seropositive Individuals," *J. Infect. Diseases* (1991) 164(3):470–475.

Letvin et al., "Infection of Baboons with Human Immunodeficiency Virus–2 (HIV–2)," *J. Infect. Diseases* (1987) 156:406–407.

Nicol et al., "Persistent HIV–2 Infection of Rhesus Macaque, Baboon, and Mangabeys," *Intervirology* (1989) 30(5):258–267.

Putkonen et al., "Experimental Infection of Cynomolgus Monkeys (Macaca Fascicularis) with HIV–2," *J. Acquired Immune Deficiency Syndromes* (1989) 2(4):366–373.

Schnittman et al., "The Reservoir for HIV–1 in Human Peripheral Blood is a T Cell that Maintains Expression of CD4," *Science* (1989) 245:305–308.

*Primary Examiner*—Bruce R. Campell

*Attorney, Agent, or Firm*—Karl Bozicevic; Fish & Richardson P.C.

[57] ABSTRACT

Strains of HIV-2 capable of infecting humans and non-human primates such as baboons and causing an immune system disease are disclosed. The HIV-2 strain are used to infect non-human primates which infected primates present symptoms of a disease of the immune system and are used to test drugs, e.g., anti-virals and/or vaccines for their ability to treat and/or prevent lentiviral infections such as HIV infections. Useful strains are HIV-$2_{UC2}$, HIV-$2_{UC12}$ and HIV-$2_{UC14}$ and preferred non-human primates are baboons.

3 Claims, 3 Drawing Sheets

HIV-2 STRAINS CAPABLE OF INFECTING HUMANS AND NON-HUMAN PRIMATES, AND INFECTED NON-HUMAN PRIMATES WITH IMMUNE SYSTEM DISEASE

GOVERNMENT SUPPORT

Research carried out in connection with the invention described herein was supported under Grant No. U01-AI26471 awarded by the National Institutes of Health. The U.S. Government may have certain rights in this invention.

FIELD OF THE INVENTION

This invention relates generally to the field of animal models useful in testing drugs and relates specifically to baboons infected with a lentivirus (specificgally HIV-2) which baboons exhibit symptoms of immune system disease.

BACKGROUND OF THE INVENTION

Despite advances in our understanding of AIDS and its etiologic agents, HIV-1 and HIV-2, there is no well-established animal model to study potential therapies and vaccines for HIV-induced diseases. Of the non-human primates, the chimpanzee (H. J. Alter, et al., *Science*, 226, 549–552 (1984); P. N. Fultz, et al., *Journal of Virology*, 58, 116–124 (1986)) and *Macaca nemestrina* (M. B. Agy, et al., *Science*, 257, 103–106 (1992)) are the major species susceptible to HIV-1 infection. Apart from some symptoms of acute infection observed in the macaque model, in neither of these systems have animals developed symptoms generally associated with immune system diseases (symptoms of AIDS). In the case of the chimpanzee, the ability to infect and cause disease, together with their endangered species status and cost, makes their use problematic. Moreover, most evidence indicates that reproducible persistent infection of *M. nemestrina* with HIV-1 strains cannot be achieved (L. R. Frumkin, et al., *Virology* 195, 422–431 (1993).

The most promising animal models presently being evaluated for studies of HIV pathogenesis and antiviral approaches are rhesus macaques infected with $SIV_{mac}$ strains (R. C. Desrosiers, *Annual Review of Immunology* 8, 557–558 (1990); M. B. Gardner, P. A. Luciw, *Federation of American Societies for Experimental Biology Journal* 3. 2593–2606 (1989)) and $SIV_{mac}$/HIV-1 chimeras (J. Li, C. I. Lord, W. Haseltine, N. L. Letvin, J. Sodroski, *Journal of Acquired Immune Deficiency Syndromes* 5, 639–646 (1992); R. Shibata, A. Adachi, *AIDS Research and Human Retroviruses* 8, 403–409 (1992)). However, despite the close relatedness of certain SIV and HIV-2 strains, results obtained using these SIV-based models may not be directly applicable to infection with a human lentivirus.

It has also been shown that specific HIV strains will infect non-human primate PBMC. (See Castro, et al., *Virology* 184, 219–226 (1991)). Other models employing HIV-2 infection of various macaque species have also been studied (J. Livartowski, et al., *Cancer-Detection and Prevention* 16, 341–345 (1992); C. Stahl-Hennig, et al., *AIDS* 6, 611–617 (1990); P. Putkonen, et al., *Journal of Acquired Immune Deficiency Syndromes* 2, 366–373 (1989)), but the virus showed pathogenicity only after serial passage through *M. nemestrina* (J. McClure, et al., Abstract, 10th Annual *Symposium on Nonhuman Primate Models for AIDS* (1992)). Therefore, an important need exists for a reproducible and affordable animal model of viral persistence and pathogenesis which can employ various HIV strains to test possible vaccine and antiviral strategies. The present invention serves that need.

SUMMARY OF THE INVENTION

The invention includes viral strains of HIV-2 which are capable of infecting humans and non-human primates and causing symptoms of disease of the immune systems, i.e. symptoms such as observed with AIDS. The viral strains are used to infect non-human primates which primates can then be used to test the efficacy of drugs (e.g., anti-virals and vaccines) to treat immune system diseases and/or prevent infection of humans with a lentivirus such as HIV, i.e. HIV-1 and HIV-2. Preferred primates are baboons infected with a lentivirus, preferably HIV-2 strains, more preferably HIV-$2_{UC2}$, HIV-$2_{UC12}$ and HIV-$2_{UC14}$. Persistent infection of baboons has been obtained with diverse strains of HIV-2. Infected animals exhibited symptoms and disease analogous to those observed in HIV-infected humans.

An object of the invention is to provide strains of HIV-2 capable of infecting a human and also capable of infecting a non-human primate (specifically a baboon) and causing an immune system disease.

Another object is to provide a non-human primate such as a baboon which exhibits symptoms of immune disease when infected with a strain of a lentivirus such as a strain of HIV-2 capable of infecting either a human or a non-human primate.

An advantage of the invention is that non-human primates of the invention (baboons infected with a pathogenic retrovirus) provide useful animal models for testing the safety and efficacy of drugs for treating human immune system diseases such as those caused by lentivirus infection and specifically HIV infection.

A feature of the invention is that animals infected with the viral strains exhibit symptoms and diseases analogous to those observed in humans infected with pathogenic retroviruses, e.g. HIV-infected humans.

These and other objects, advantages and features of the invention will become apparent to those skilled in the art upon reading the details of the invention as described herein.

DETAILED DESCRIPTION OF THE INVENTION

Figure 1:
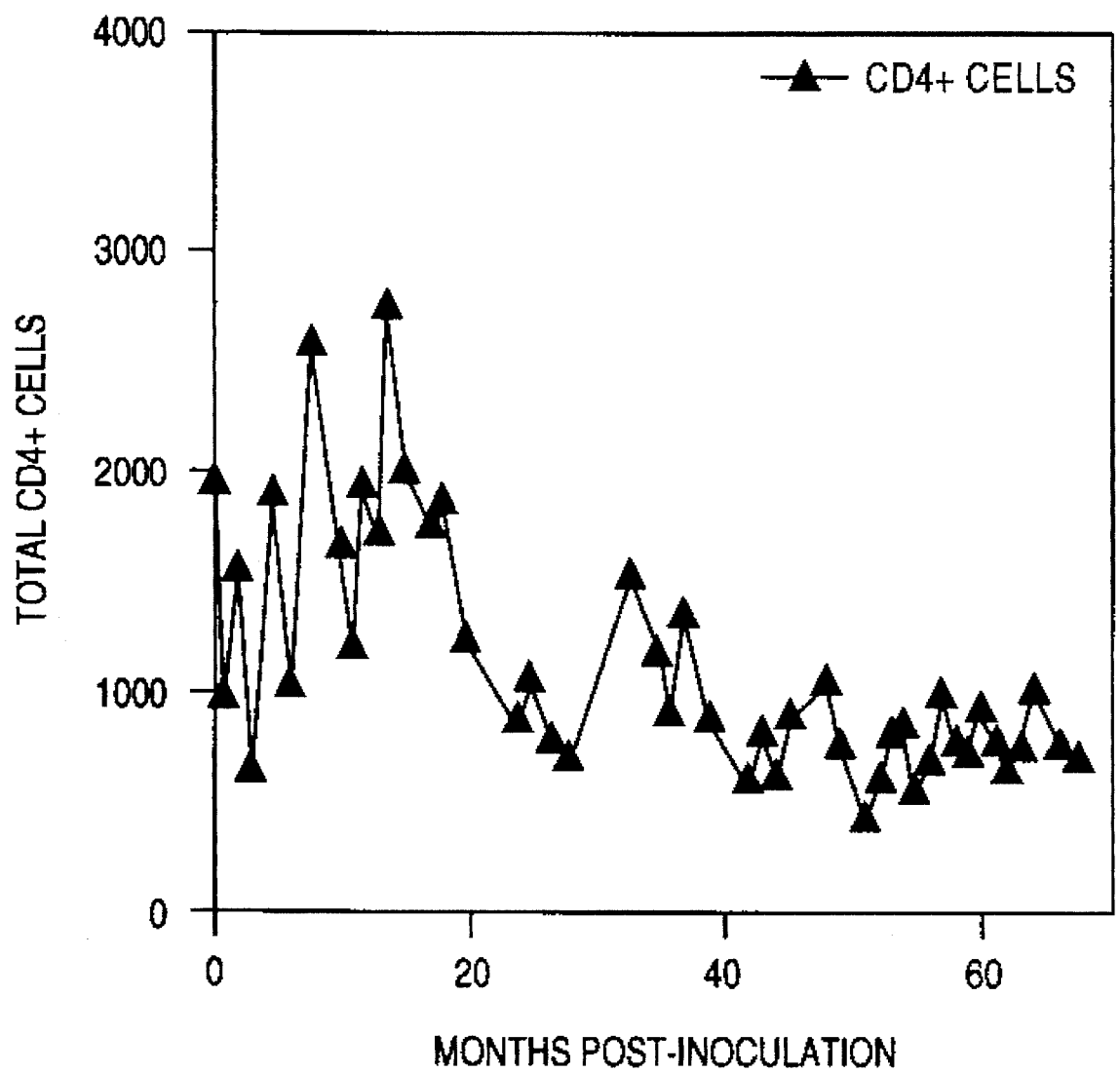
In FIG. 1 is a graph wherein the total number of CD4+ cells in a baboon (#1) is plotted over time from the point of inoculation with HIV-2.

Before the present non-human primates infected with a lentivirus such as HIV-2 and expressing symptoms of immune system diseases are described it is to be understood that the non-human primates, baboons, and viral strains are not limited to the specific embodiments disclosed herein as such may, of course, vary. It is to be understood that the terminology used herein is for the purpose of describing particular embodiments only, and is not intended to be limiting since the scope of the present invention will be limited only by the appended claims.

As used in this specification and the appended claims, the singular forms "a" and "the" include plural referents unless the context clearly dictates otherwise. Thus, for example, reference to "infecting a baboon with a virus" includes infecting the baboon with a large number of viruses and or different strains of viruses capable of infecting the baboon, reference to "the formulation" or "the method" includes one or more formulations, methods and/or steps of the type described herein and or which will become apparent to those skilled in the art on reading this disclosure and so forth.

All publications cited herein are incorporated by reference to disclose and describe the subject matter for which they are cited in connection with.

The term "symptom of immune disease" shall be interpreted to mean symptoms generally associated with immune system diseases by those skilled in the art and in particular symptoms associated with humans infected with lentiviruses and more particularly with human AIDS patients which symptoms include all or any of lymphadenopathy, hepatosplenomegaly, lymphocytopenia, thrombocytopenia, anemia, skin lesions, fibromatosis, cachexia and ulcerative gingivitis which does not respond to antibiotic treatment.

The term "immune system disease" shall mean a disease of the immune system of a human or a non-human primate which disease is caused by infection with a lentivirus (specifically HIV) and results in all or any of the symptoms described above. Immune system diseases are generally associated with the diseases which cause, over time, a reduction in the number of CD4+ cells. A reduction of 20% or more below normal levels indicates a compromised immune system in the presence of immune disease.

The term "HIV-2 formulation" shall mean a composition comprised of an active lentivirus which is a pathogenic human retrovirus (preferably active HIV-2) in a pharmaceutically acceptable carrier wherein the viral strain (e.g. HIV-2 strain) is capable of infecting a human and capable of infecting a non-human primate (baboons) and causing an immune system disease. The formulation is used to inoculate non-human primates to create useful animal models.

The term "$TCID_{50}$" is an abbreviation for tissue culture infectious dose 50-dilution at which one-half of the cultures inoculated with viruses became infected.

The term "PBMC" is an abbreviation for peripheral blood mononuclear cells.

The term "PHA" is an abbreviation for phytohemagglutinin which is added to the process to make base cells in a culture more susceptible to infection with the virus.

The invention includes several different aspects. One aspect of the invention is the isolated viral strains of a lentivirus, preferably HIV-2 which strains are capable of infecting humans and causing a disease of the immune system and also capable of infecting non-human primates and causing disease of the immune system which disease presents symptoms similar to the symptoms observed with HIV infected humans. The infected baboons of the invention have infections which are both persistent and pathogenic. Another aspect of the invention is a non-human primate and specifically a baboon infected with a lentivirus, preferably HIV-2 which primates develop immune diseases and show symptoms of such diseases. The infected non-human primates are used for animal models for the testing of drugs including anti-viral drugs which might be effective in the treatment of infected humans or non-human primates and vaccines which might prevent humans and/or non-human primates from being infected with a lentivirus such as HIV, specifically HIV-1 and HIV-2.

We have found two HIV-2 strains from the Ivory Coast (HIV-2$_{UC2}$ and HIV-2$_{UC3}$, referred to here as UC2 and UC3) that readily infected cultured baboon PBMC and produced persistent infection in the baboons. Of the two viral strains, UC2 appeared to induce the longest period of persistent infection (baboon #1 HIV-2$_{UC2}$ infected baboon of Table 1).

For almost four years, beginning at 18 months post-inoculation, one baboon (baboon #1 of Table 1) had persistent viremia and exhibited a continuous decline in total CD4+ T lymphocytes (FIG. 1). The data shown in FIG. 1 as regards to the total number of CD4+ cells was obtained in accordance with the procedures described with respect to Table 1 below. The HIV-2 specific antibody titers are expressed as the highest dilution of plasma that gave a positive result. The HIV-2 antibody levels were measured using the Detect HIV 1–2 antibody ELISA kit (available from Coulter, Hialeah, Fla.—the "+" indicates positive virus culture whereas the "−" indicates negative virus culture). The viruses were isolated in accordance with the procedures described within Table 1.

Based on the results as per FIG. 1, additional baboons were inoculated with the UC2 strain, and experiments were carried out to identify other lentiviral strains, specifically HIV-2 strains for animal inoculation. The experiments involved in vitro pre-screening in baboon PBMC which identified two other HIV-2 strains, UC12 and UC14, (recovered from patients in Gambia) that grew efficiently and consistently in cultured baboon PBMC. The UC2 strain grew well in the PBMC of 13 of 13 (100%) of the baboons tested, UC12 grew in 11/13 (84.6%) and UC14 in 13/13 (100%).

Four additional baboons (#s 2, 3, 4 and 5 of table 1) were given an intravenous inoculation of approximately 5000 $TCID_{50}$ (measured in human PBMC) of UC 2. Within two weeks following virus inoculation, all four of these animals developed widespread lymphadenopathy (see Table 1 below), which persisted for at least 20 weeks.

Although intravenous inoculation is preferred the non-human primates can be inoculated by other means provided the virus material enters the bloodstream of the animal. Further, although the specific non-human primates which were inoculated in accordance with the above-described procedure (all received a 5,000 $TCID_{50}$ of HIV-2$_{UC2}$) it is possible to administer different amounts of virus. The amount will vary somewhat depending on a particular viral strain and the size and type of non-human primate being inoculated. Workable variations in the amount and means of administration will be apparent to those skilled in the art upon reading this disclosure.

An aspect of the invention may be carried out by first creating a lentivirus formulation (specifically an HIV formulation) comprised of active lentivirus (specifically active HIV-2) in a carrier such as a saline solution. A unit dose of such formulation may include 1,000 to 20,000 $TCID_{50}$ of active lentivirus (e.g. active HIV-2) in 1 to 20 cc of carrier. The formulation is injected into a non-human primate (baboon) and the animal is observed to determine if the animal presents symptoms such as the symptoms frequently observed in humans acutely infected with HIV.

Another aspect of the invention is an inoculation kit which includes a plurality of doses of formulation premeasured to be administered to a particular animal (preferably a baboon) along with instructions for inoculation and/or observing the animal after inoculation for symptoms of immune disease.

TABLE 1

HIV-2 Inoculation of Baboons

| Inoculation dated | Baboon (subspecies) | Inoculum | Infection status | Clinical status (time of initial signs) |
|---|---|---|---|---|
| 9/16/88 | #1 (PCA) | UC2 | Persistent infection | CD4+ cell decline (18 mo.) |
| 1/23/92 | #4 (PCH) | UC2 | Persistent infection | CD4+ cell decline (16 mo); lymphadenopathy (2 wk); AIDS-like syndrome (28 mo) |
|  | #3 (PCH) | UC2 | Persistent infection | CD4+ cell decline (28 mo); lymphadenopathy (2 wk); AIDS-like symptoms at 30 months |
|  | #2 (PCH) | UC2 | Intermittent virus isolation | lymphadenopathy (2 wk) |
|  | #5 (PCX) | UC2 | Transient virus isolation | lymphadenopathy (2 wk) |
|  | #6 (PCH) | Control | Uninfected |  |
| 1/25/93 | #7 (PCX) | UC14 | Transient virus isolation plasma viremia (2 wk) | transient CD4+ cell decline (4–8 mo) |
|  | #8 (PCH) | UC14 | Intermittent virus isolation viremia (2, 6, 8 wk) |  |
|  | #9 (PCH) | UC14 | Intermittent virus isolation |  |

Table 1. HIV-2 inoculation of Papio cynocephalus baboons

The animals used to obtain the results described in Table 1 were young adult baboons (4–9 years old). Subspecies designations are: PCA, *Papio cynocephalus anubis*; PCH, *Papio cynocephalus hamadrayas*; PCX, *Papio cynocephalus anubis/cynocephalus hamadrayas*. Those skilled in the art will recognize that lentivirus strain (preferably the HIV-2 strains such as the strains disclosed herein) can be administered as indicated herein to a variety of different non-human primates. After administering the viral strains the animals can be observed over time for the presentation of symptoms of the type described herein. When symptoms occur over time those animals can also be judged as being useful as animal models for testing the human efficacy and safety of drugs such as antivirals or vaccines which treat or prevent lentiviral infection (specifically treat or prevent HIV infection).

Persistent infection indicates positive virus cultures from the PBMC at almost all timepoints (>90%); intermittent virus isolation indicates positive virus cultures at more than one time point following acute infection (0–20 weeks) and at least one positive isolation within the last 4 months; transient isolation indicates virus recovery only during acute infection.

In order to obtain the results tabulated in Table 1, the baboons were inoculated intravenously with 5000 $TCID_{50}$ of UC2 or 10,000 $TCID_{50}$ of UC14 on the date shown in the first column of Table 1. HIV-2 strains were prepared and titrated in human PBMC obtained from human seronegative donors (S. W. Barnett, M. Quiroga, A. Werner, D. Dina, J. A. Levy, *Journal of Virology*, 67, 1006–1014 (1993)). The PBMC from all animals were prescreened for in vitro susceptibility to virus infection (see Castro et al. cited above). All inoculations and animal manipulations were performed according to NIH guidelines at the Southwest Foundation for Biomedical Research (incorporated herein by reference). Every two weeks for 12 weeks, then at four-week intervals, animals were sedated with ketamine hydrochloride (10 mg/kg) and examined for hepato- or splenomegaly, lymphadenopathy, fever, weight loss and cutaneous symptoms. At these times, venipuncture was performed and blood specimens collected.

Virus isolations were performed by cocultivation of the PBMC of infected animals with PHA-stimulated PBMC from seronegative human donors (see Castro, et al.). Culture supernatants were monitored for virus at 3–4 day intervals using either the HIV-1 p24 ELISA (available from Coulter, Hialeah, Fla.) or the RT (reverse transcriptase) assay (A. D. Hoffman, B. Banapour, J. A. Levy, *Virology* 147, 326–335 (1985)). In some cases, CD4+ baboon PBMC were purified using anti-CD4 immunomagnetic beads (available from Dynal, Lake Success, N.Y.) prior to cocultivation with human PBMC (C. E. Mackewicz, H. W. Ortega, J. A. Levy, *Journal of Clinical Investigation*, 87, 1462–1466 (1991)). Fresh plasma specimens were assayed for infectious virus within 3 hours after collection by inoculation onto human PBMC (L. Z. Pan, A. Werner, J. A. Levy, *Journal of Clinical Microbiology* 31, 283–288 (1993)). T-cell subsets were measured by flow cytometry using the leu 3a (CD4), and leu 2a (CD8) monoclonal antibodies available from (Becton Dickinson, San Jose, Calif.).

Results Demonstrated by Table 1.

At one year post-inoculation, lymph node sections taken from one animal, (#3 of table 1), revealed a mixed cellular hyperplasia which included follicular hyperplasia, paracortical hyperplasia, and infiltration of the medullary cords with plasma cells. Follicular hyperplasia is also commonly observed during the early stages of HIV and SIV infections (L. V. Chalifoux, et al., *American Journal of Pathology*, 128, 104–110 (1987); D. J. Ringler, et al., *American Journal of Pathology* 134, 373–383; M. S. Wyand, et al., *American Journal of Pathology*, 134, 385–393 (1989); P. Racz Tenner-Racz, K. C. Kahl, et al., *Progress in Allergy*, 37, 81–181 (1986)).

Figure 2:
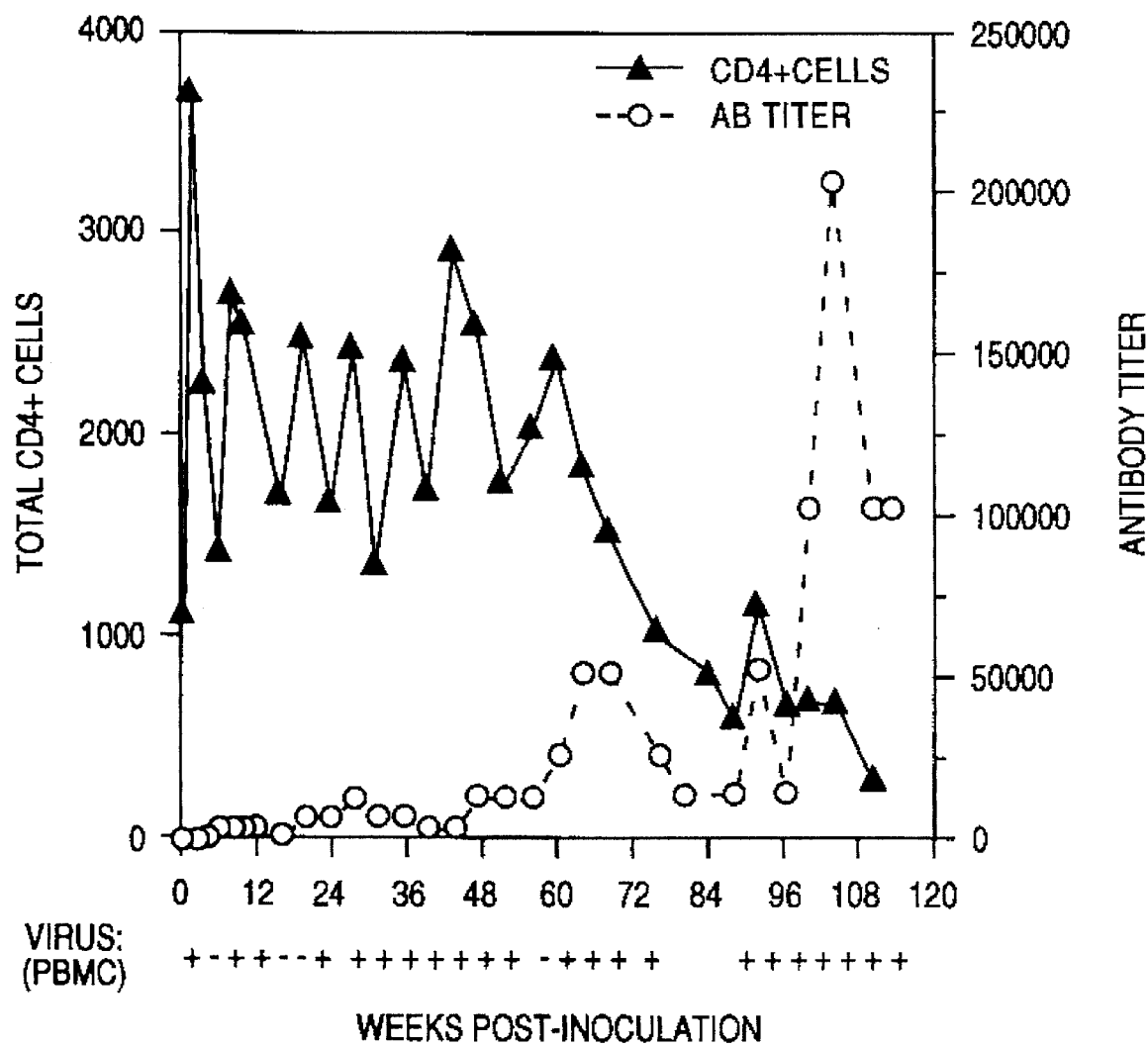
FIG. 2 is a graph wherein the total number of a CD4+ cells in another baboon (#2) and anti-HIV antibody production are plotted over time from the point of inoculation with HIV-2 (the results given below indicate frequent isolation of the virus from the baboon)
Figure 3:
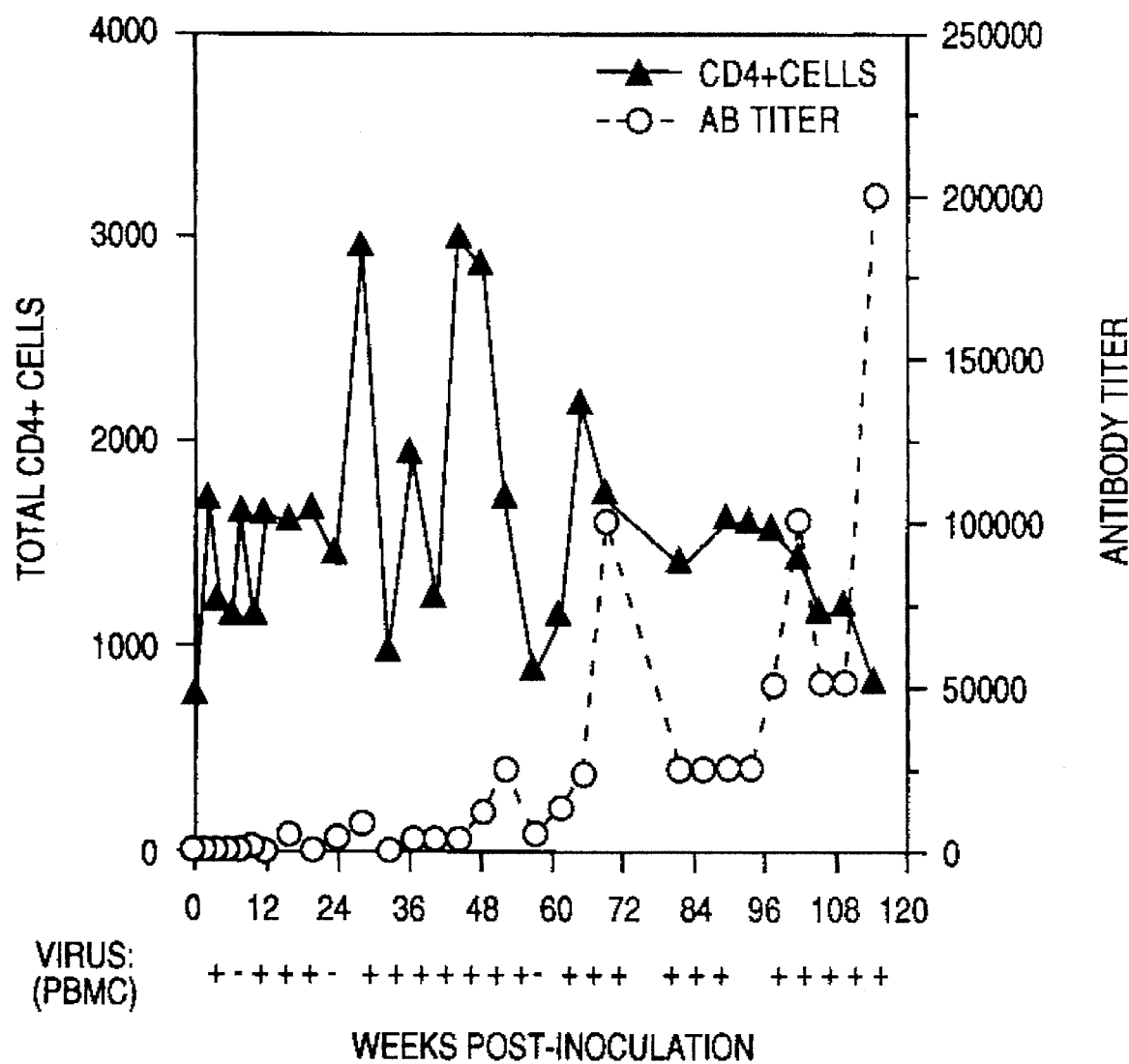
FIG. 3 is a graph wherein a total number of a CD4+ cells in yet another baboon (#3) and anti-HIV antibody production are plotted over time from the point of inoculation with HIV-2 (the results given below indicate frequent isolation of the virus from the baboon).

Infectious virus was recovered from the PBMC of all four UC2-inoculated baboons as early as two weeks post-inoculation. Positive virus cultures were repeatedly demonstrated in three of the animals (#s 2, 3 and 4) (Table 1; FIGS. 2 and 3). The PBMC from the fourth animal, #5, was shown to harbor provirus as late as 44 weeks post-inoculation as determined by DNA PCR analysis. Seroconversion was observed in the baboons at 4–6 weeks after virus inoculation (FIGS. 2 and 3). Western blot analysis of sera from three of the UC2-infected baboons showed reactivity to all the major HIV-2 viral proteins within 12 to 20 weeks; the other baboons (#5) demonstrated only limited reactivity to p27 gag.

Starting at about 65 weeks post-inoculation, a dramatic loss of CD4+ T lymphocytes was observed in baboon #4 (FIG. 2). During the following six months this animal's total CD4+ T cells dropped from an average of 2000 cells/$mm^3$ to only 600 cells/$mm^3$, and its CD4/CD8 ratio decreased from an average of 1.5 to 0.3. During the same time period, the uninfected control baboon #6 exhibited an average of about 1600 CD4+ cells/mm$^3$ with a CD4/CD8 ratio of about 1.6. Moreover, approximately two years post-inoculation with UC2, baboon #4 presented with marked lymphadenopathy, hepatosplenomegaly, lymphocytopenia, thrombocytopenia, severe anemia, skin lesions (e.g. alopecia), and ulcerative gingivitis which did not respond to antibiotic treatment. Animal #4 was subsequently euthanized and its tissues were examined at necropsy. Total CD4+ peripheral lymphocytes at time of necropsy were at 275 cells/mm$^3$. A decrease of 20% or more from normal CD4+ levels is an indication of infections with the HIV-2 strain and immune system disease.

Histopathologic examination of the lymph nodes of animal #3 revealed evidence of follicular lysis and paracortical cell expansion. Immunohistochemical staining with cell-specific anti-CD20 antibody demonstrated lymphoid depletion in the germinal centers of the lymph nodes from this animal. Follicular depletion is characteristic of the later stages of HIV and SIV-induced disease in human and macaques, respectively (L. V. Chalifoux, et al., *American Journal of Pathology*, 128, 104–110 (1987); D. J. Ringler, et al., *American Journal of Pathology* 134, 373–383; M. S. Wyand, et al., *American Journal of Pathology*, 134, 385–393 (1989); P. Racz Tenner-Racz, K. C. Kahl, et al., *Progress in Allergy*, 37, 81–181 (1986)).

Loss of the function of the follicular dendritic cell network could lead to increased viremia in the blood and rapid progression to disease in HIV-infected individuals (G. Pantaleo, et al., *Nature* 362, 355–358; J. Embretson, et al., *Nature* 362, 359–362 (1993)). This pathogenic process could explain the relatively high levels of infectious virus found in the PBMC of HIV-2-infected baboon #4 just prior to and at the time of necropsy (see Table 2 below).

TABLE 2

Detection of HIV-2 in lymphoid tissues and PBMC from infected baboons

| Animal | Virus | Week | Tissue | Infectious center titer | % CD4+ cells |
|---|---|---|---|---|---|
| Biopsy specimens: | | | | | |
| #4 | UC2 | 111 | LNC-ing. | 10$^3$ | 16.4 |
| | | | PBMC | 10$^3$ | 16.0 |
| #3 | UC2 | 119 | LNC-ing. | + | 53.0 |
| | | | PBMC | 10$^3$ | 29.4 |
| #2 | UC2 | 119 | LNC-ing. | – | 42.0 |
| | | | PBMC | – | 27.4 |
| #5 | UC2 | 119 | LNC-ing. | – | 59.0 |
| | | | PBMC | – | 25.7 |
| #8 | UC14 | 58 | LNC-ing. | 10$^3$ | 55.0 |
| | | | PBMC | 10$^6$ | 32.8 |
| #6 | not infected | 111 | LNC-ing. | – | 60.9 |
| | | | PBMC | | 51.2 |
| Necropsy specimens: | | | | | |
| #4 | UC2 | 114 | spleen | + | 1.97 |
| | | | thymus | + | 46.08 |
| | | | LNC-cerv. | 10$^3$ | 15.36 |
| | | | LNC-med. | 10$^4$ | 14.95 |
| | | | LNC-ing. | 10$^4$ | 12.03 |
| | | | LNC-ax. | 10$^3$ | 15.6 |
| | | | LNC-mes. | + | 12.02 |
| | | | PBMC | 10$^3$ | 10.94 |

Table 2. Detection of HIV-2 in lymphoid tissues and PBMC from infected baboons

Lymph node cells (LNC) were recovered from the inguinal (ing.), cervical (cerv.), mediastinal (med.), axillary (ax.), and mesenteric (mes.) lymph nodes at the indicated times post-inoculation. Infectious center assays were performed by cocultivating these LNC or baboon PBMC at varying cell densities (10$^2$–10$^6$ cells) with 10$^6$ PHA-stimulated human PBMC in a 24-well plate. Infectious center titers represent the lowest cell density of baboon cells that yielded a positive virus culture. + indicates a positive virus culture when 3×10$^6$ cells were cocultured with human PBMC; – indicates no virus recovery from a similar culture. Culture supernatants were monitored for virus at 3–7 day intervals using either then HIV-1 p24 ELISA (Coulter, Hialeah, Fla.) or the RT (reverse transcriptase) assay (see Hoffman et al. cited above). The percentage of CD4+ cells was determined as described above with reference to Table 1.

The percentages of CD4+ cells in the lymph nodes of #4 were dramatically reduced as compared to those of the other infected animals and the uninfected control (Table 2). This reduction was observed at 3 weeks prior to and at the time of necropsy. In macaques infected with SIV, a decline in lymph node CD4+ cells is not generally observed until the final stages of disease when circulating CD4+/CD8+ cell ratios have fallen to 0.5 or below. This observation is believed to be indicative of the immunological deterioration of the lymph node that eventually leads to increased susceptibility to infections and progression to simian AIDS (Y. J. Rosenberg, et al., *AIDS Research and Human Retroviruses* 9, 639–646 (1993). In that baboon #4 was observed to follow a similar course of diagnosed events as compared to animal (simian or human) with AIDS it can be concluded that a baboon infected with HIV-2$_{UC2}$, HIV-2$_{UC12}$ and HIV-2$_{UC14}$ can serve as a useful animal model for the testing of anti-virals and vaccines. Formulation of these viral strains in the form of pre-measured unit doses provided with instructions on the inoculation of baboons are useful kits of the invention.

In addition to the specific HIV strain described here, other lentiviral strains and specific other pathogenic retroviral strains such as HIV-2 strains can be used if the strains are capable of infecting humans and causing a disease of the immune system and capable of infecting the non-human primate and resulting in immune system diseases. Those skilled in the art can follow the disclosure provided herein with respect to specific examples and apply those to other lentiviral strains and specifically other strains of HIV-2 and other non-human primates in order to develop other useful animal models which can be used to test the effectiveness of drugs such as anti-virals or vaccines for the treatment or prevention of lentiviral (specifically HIV) infection, respectively.

It is noteworthy that extensive fibrosis was observed in the skin, lymph nodes, thyroid, and pancreas of baboon #4. This condition appears to be an abnormal hyperplasia characterized by vasocentric proliferation of fibroblast-like cells in the tissues. A similar condition can be observed with fibrous tumors in HIV-infected humans. This type of tumor has not been reported previously in baboons. A similar fibrosis (retroperitoneal fibromatosis) has been described in macaques with SAIDS associated with infection with the simian retrovirus, SRV-2 (K. Stromberg, et al., *Science* 224, 289–292 (1984); P. A. Marx, et al., *Journal of Virology* 56, 571–578 (1985)). The condition in the macaques has been considered analogous to Kaposi's sarcoma in HIV-infected humans (see Stromberg, et al.). It should be noted that serologic evaluation of baboon #4 showed no evidence of infection with STLV or SRV-2.

Histopathologic examination of lung tissue from animal #4 also showed evidence of lymphocytic interstitial pneumonitis. This disease is characterized by lymphocyte (CD8+) infiltration of the lung and is common in HIV-infected children. This disease alone could have been fatal to this animal if it had not been sacrificed.

Finally, lymph node cells (LNC) and PBMC taken from baboon #4 three weeks before and at the time of necropsy had appreciable virus loads relative to the other infected baboons (see Table 2). Virus was isolated from the cells of all lymphold tissues examined including mesenteric, axillary, mediastinal, and cervical lymph nodes, spleen, bone marrow, and PBMC. Just prior to sacrifice, 1 in 1000 PBMC and 1 in 1000 LNC from this animal were found to harbor infectious virus. This amount represents about 1 in 160 infected CD4+ cells in these tissues at this time. These values are comparable to those observed during the later stages of HIV disease in humans (K. Hsia, S. A. Spector, *Journal of Infectious Diseases* 164, 470–475 (1991); S. M. Schnittman, et al., *Science* 245, 305–308 (1989)). Immunohistochemical examination has further shown viral gp130 and p27 in macrophages in the lymph node, colon and spleen. This widespread HIV-2 infection of tissues in this animal is an additional feature that resembles end-stage HIV and SIV-induced diseases in their respective hosts (Y. K. Donaldson, et al., *Lancet* 343, 382–385 (1994); V. M. Hirsch, P. M. Zack, A. P. Vogel, P. R. Johnson, *Journal of Infectious Diseases*, 163, 976–988 (1991). This evidence confirms that baboons infected with HIV-2 strains UC2, UC12 and UC14 provide good animals models for the testing of drugs (e.g. antivitals and vaccines) which could be effective in treating humans infected with a lentivirus such as HIV or preventing and/or hindering infection.

Baboon #3, another animal in the same group of UC2-infected animals, also has demonstrated a noticeable decline in its CD4+ cells (and CD4+/CD8+ cell ratio) after 69 weeks (FIG. 3). As observed in the case of animal #4, this decline appeared to correspond to a sharp rise in HIV-2 specific antibody titers in this animal. Moreover, a lymph node biopsy specimen taken from baboon #3 at 119 weeks post-inoculation revealed an enlarged lymph node that showed mixed cellular hyperplasia with evidence of follicular involution. When observed at 149 weeks the animal showed lymph node depletion and had multiple skin fibrous lesions. Further, the animal was generally diagnosed with cachexia (failure to thrive). The animal showed definitive AIDS-like symptoms at 30 months. These findings are predictive of a clinical course similar to that observed for baboon #4.

In further studies evaluating the baboon as an experimental model of HIV infection, three additional baboons (#7, #8, #9) were inoculated intravenously with 10,000 TCID$_{50}$ of HIV-2$_{UC14}$ (Table 1). Virus was recovered from the PBMC of each animal at week two, and intermittently thereafter from baboons #8 and #9. Moreover, in two of these animals (#7 and #8) infectious virus was isolated from the cell-free plasma during acute infection indicating extensive replication of UC14 in the baboon. All animals seroconverted in 2–4 weeks. The successful infection of these baboons with a second and entirely different strain of HIV-2 lends support to the potential usefulness of this animal model for vaccine studies that required heterologous virus challenge.

The scope of the present invention can be expanded to include the serial passage of viruses from both UC2 and UC14-infected baboons into additional animals and thereafter selecting for viral variants that induce a more rapid pathogenic course. As an example of such, blood was transfused from animals #4 (UC2-infected) and #8 (UC14-infected) into each of two naive baboons. Both animals seroconverted and virus has been recovered consistently from their PBMC from 2 weeks to the present time (20 weeks). Furthermore, one of these animals (#10; UC2-infected) showed plasma viremia at week 8. The lymph node of the other animal (#11: UC14-infected) revealed virus infection by culture at this time point.

Thus, another aspect of the invention involves infecting different non-human primates with different strains and combinations of strains of lentiviruses such as HIV, in particular, HIV-2. Thereafter, the infected animals are observed and those developing more rapid and more severe symptoms of immune system disease are selected and the strain or strains which infected them are determined as preferred strains for creating animal models of the invention. The viral variants created in the infected animals may be particularly useful in creating further animal models. The blood from different infected baboons can be mixed and the mixtures can be used to create still other animal models.

In summary, baboons have been successfully infected with two different strains of HIV-2. These infections have been characterized by frequent virus isolations from the PBMC and lymph nodes, lymphadenopathy, plasma viremia, and high HIV-2-specific antibody titers. The observations indicate viral persistence in most of these animals. In three cases, a decline in total CD4+ cells was observed at about 18 months post-inoculation. In two baboons with a high virus load in the PBMC, widespread infection of lymphoid tissues, and a dramatic loss of CD4+ lymphocytes, clinical signs and symptoms including extensive fibromatosis were observed. These features closely resemble those observed in human and simian AIDS. Other investigators have shown that baboons are susceptible to infection with HIV-2 strains (N. L. Letvin, et al., *Journal of Infectious Diseases* 156, 406–407 (1987); I. Nicol, et al., *Intervirology*, 30, 258–267 (1989)), but this is the first report of viral persistence and pathogenesis observed in this animal. HIV-2 infection of baboons offers a promising, reproducible, and affordable animal model for studies of HIV persistence and pathogenesis, and for evaluating antiviral approaches. Further, vaccines can be tested by administering the vaccines to a baboon and thereafter attempting infection of the vaccinated baboon with the HIV-2 strains UC12 and UC14. If no infection is observed the vaccine can be deduced as having prevented infection of a primate with an HIV strain which normally infects that primate.

Deposits

The viral strains HIV-2$_{UC2}$, (ATCC designation VR 2468) HIV-2$_{UC12}$, (ATCC designaation VR 2469) and HIV-2$_{UC14}$ (ATCC designation VR 2470) have been deposited with the American Type Culture Collection (ATCC), Rockville, Md., U.S.A. for patent purposes. The viral strains were deposited on Aug. 4, 1995 under conditions specified by the Budapest Treaty on the international recognition of the deposit of microorganisms (Budapest The present invention has been disclosed and described herein and was considered to be the most practical and preferred embodiments. It is recognized, however, that departures may be made therefrom which are within the scope of the invention, and that modifications will occur to one skilled in the art upon reading this disclosure.

What is claimed is:

1. A method for testing the efficacy of a drug in the treatment of infection with HIV, comprising:

administering the drug to a baboon infected with HIV-2$_{UC2}$, wherein HIV-2$_{UC2}$ is also capable of infecting a human and further wherein the infected baboon exhibits symptoms of an immune system disease associated with HIV infection in humans, which symptoms are persistent and pathogenic; and observing the baboon to determine if the drug prevents or decreases the presentation of symptoms associated with infection with HIV-$2_{UC2}$;

wherein the baboon is of a subspecies selected from the group consisting of Papio cynocephalus hamadrayas, and Papio cynocephalus anubis/cynocephalus hamadrayas.

2. The method of claim 1, wherein the symptoms are selected from the group consisting of lymphadenopathy, hepatosplenomegaly, lymphocytopenia, thrombocytopenia, anemia, skin lesions, fibromatosis, cachexia and ulcerative gingivitis, which symptom does not respond to antibiotic treatment.

3. A method for testing the efficacy of a drug in the treatment of infection with HIV, comprising:

administering the drug to a baboon infected with HIV-$2_{UC14}$, wherein the HIV-$2_{UC14}$ is also capable of infecting a human and further wherein the infected baboon exhibits a symptom of an immune system disease which symptom is CD4+ cell depletion; and observing the baboon to determine if the drug prevents or decreases the presentation of symptoms associated with infection with HIV-$2_{UC14}$;

wherein the baboon is of a subspecies selected from the group consisting of Papio cynocephalus hamadrayas, and Papio cynocephalus anubis/cynocephalus hamadrayas.

* * * * *